United States Patent [19]

Filler

[11] Patent Number: 4,890,603
[45] Date of Patent: Jan. 2, 1990

[54] EXTRACORPOREAL SHOCK WAVE LITHOTRIPSY EMPLOYING NON-FOCUSED, SPHERICAL-SECTOR SHOCK WAVES

[76] Inventor: William S. Filler, 7420 Westlake Ter. No. 1402, Bethesda, Md. 20817

[21] Appl. No.: 118,325

[22] Filed: Nov. 9, 1987

[51] Int. Cl.$^4$ .............................................. A61B 17/22
[52] U.S. Cl. ...................................................... 128/24 A
[58] Field of Search ............. 128/24 A, 328; 181/116, 181/118, 401; 367/145; 73/35, 12

[56] References Cited

U.S. PATENT DOCUMENTS

| | | | |
|---|---|---|---|
| 3,184,955 | 5/1965 | Filler | 73/35 |
| 3,275,098 | 9/1966 | Filler | 181/5 |
| 3,521,725 | 7/1970 | Filler et al. | 181/5 |
| 3,942,531 | 3/1976 | Hoff et al. | 128/328 |
| 4,311,147 | 1/1982 | Hausler | 128/328 |
| 4,526,168 | 7/1985 | Hassler et al. | 128/303 |
| 4,530,358 | 7/1985 | Forssmann et al. | 128/328 |
| 4,539,989 | 9/1985 | Forssmann et al. | 128/328 |
| 4,608,979 | 9/1986 | Breidenthal et al. | 128/303.1 |
| 4,617,931 | 10/1986 | Dory | 128/328 |
| 4,620,545 | 11/1986 | Shene et al. | 128/328 |
| 4,622,969 | 11/1986 | Forssmann et al. | 128/328 |

FOREIGN PATENT DOCUMENTS 0131653 1/1985 European Pat. Off. .
0155028 9/1985 European Pat. Off. .

OTHER PUBLICATIONS

William S. Filler, "Propagation of Shock Waves in a Hydrodynamic Conical Shock Tube", *The Physics of Fluids*, vol. 7, No. 5, May 1964, pp. 664–667.
A. Coombs et al., "An Underwater Explosive Shock Gun", *J. Fluid Mech.* (1967), vol. 29, Part 2, pp. 373-383.
William S. Filler, "Shock Beaming Capabilities of Hydrodynamic Conical Shock Tubes", *The Journal of the Acoustical Society of America*, vol. 50, No. 5 (part 2), 1971.
P. T. Hunter et al., "Measurement of Shock Wave Pressures Used for Lithotripsy", *The Journal of Urology*, vol. 136, Sep., pp. 733-738 (1986).
Fuchs et al., "Extracorporeal Shock-Wave Lithotripsy: An Update", *Endourology*, vol. 2 (1987), No. 2, pp. 1-8.
Kuwahara et al., "Extracorporeal Stone Disintegration Using Chemical Explosive Pellets as an Energy Source of Underwater Shock Waves", Jnl. of Urology (1986), vol. 136, pp. S14–S17.

Primary Examiner—Ruth S. Smith
Attorney, Agent, or Firm—Saidman, Sterne, Kessler & Goldstein

[57] ABSTRACT

A conical sector shock tube generates a sector of a classical diverging spherical shock wave which emanates radially from an effective point source in a nonfocusing but highly directional manner. A compression front having a radius of curvature equal to its separation from the apex of the sector shock tube defines the leading edge of a "cap shock" of accurately controllable and predictable intensity. A trailing rarefaction front of the cap shock is defined by the diffraction caused by the rim of the sector shock tube. The rarefaction front progressively erodes the cap shock as it is projected toward the target calculus, defining the width and duration of the propagating cap shock. The cap shock uniformly pulverizes the target calculus in a comparatively small quantity of shock wave applications, as compared with the larger (two orders of magnitude greater) number of shots employed in known ellipsoidal focused shock wave methods.

14 Claims, 6 Drawing Sheets

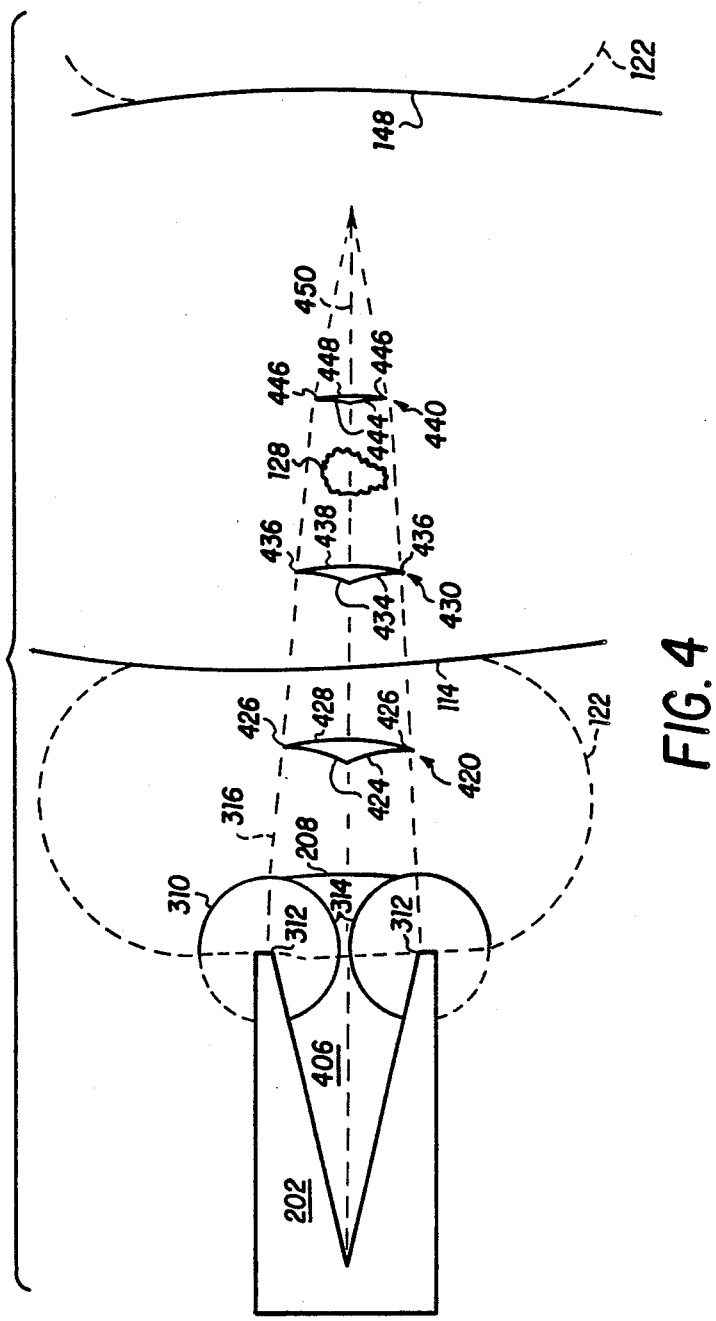

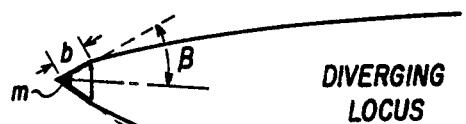
FIG. 5A
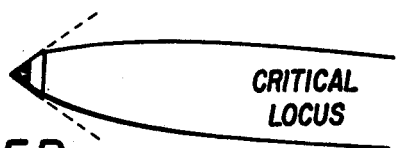
FIG. 5B
FIG. 5C
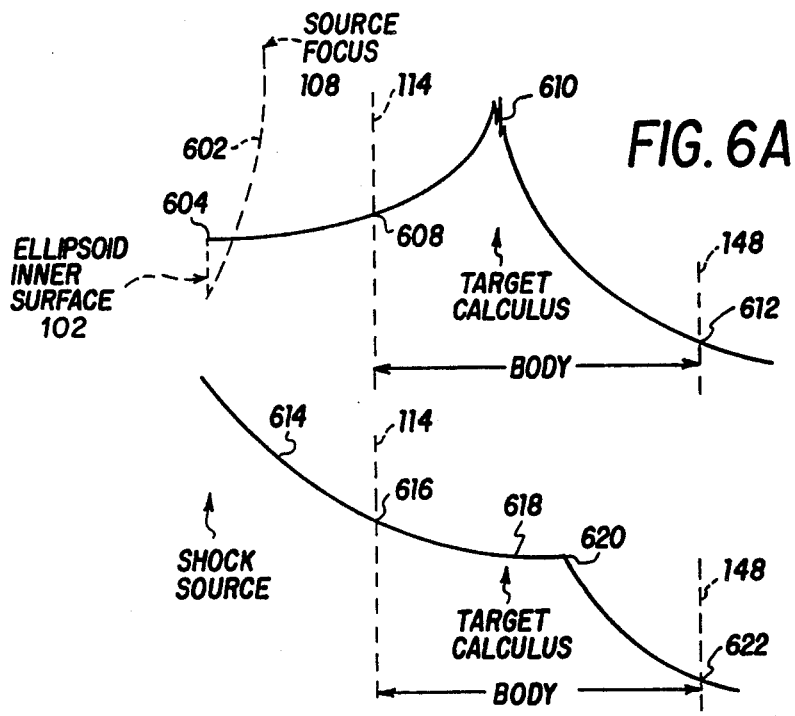
FIG. 6A PRIOR ART
FIG. 6B

EXTRACORPOREAL SHOCK WAVE LITHOTRIPSY EMPLOYING NON-FOCUSED, SPHERICAL-SECTOR SHOCK WAVES

BACKGROUND OF THE INVENTION

1. Field of the Invention

The invention relates to devices and methods for performing Extracorporeal Shock Wave Lithotripsy (ESWL). More specifically, the invention relates to methods and devices for performing ESWL in which a spherical-sector shock wave (non-focused and diverging) is applied to non-invasively disintegrate kidney stones, gallstones or other calculi within living bodies.

2. Relates Art

There are various known methods for destroying stone-like concretions (or "calculi") within living bodies using shock waves generated outside the body.

a. Ellipsoidal Shock Wave Focus Method

The first of these methods is the ellipsoidal shock focus method, which is illustrated in FIG. 1. An ellipsoid is formed by the inner surface 102 of ellipsoidal shock focus element 112 as well as by an imaginary continuation of the ellipsoidal curve along a dotted line indicated as 104, separated by circular rim 106.

Ellipsoid 102/104 has two foci. At the first, "source focus" 108 of the ellipsoid 102/104 is located a shock source such as high explosive or electrodes in a fluid medium 116. At the second, "target focus" 110 of the ellipsoid 102/104, is located the target calculus 128. In an early embodiment, the entire portion of a body 130 containing the target calculus 128 was immersed in a bath 118 having sides 124. In later embodiments, the large bath with sides 124 was replaced by a shock transfer pad or body surface shock mitigator belt 122.

In operation, the shock source located at source focus 108 is activated. This activation is accomplished by exploding a small charge of high explosive using means commonly known in the art, or by applying a high electrical potential 136 across electrode 132 and 134 so as to cause an arc and a gas generation reaction which creates a shock wave that emanates from source focus 108.

Whichever particular means of shock source is employed, a shock wave front emanates from source focus 108 in all directions. That portion of the spherical shock front which intersects that inner face 102 of ellipsoidal shock focus element 112 reflects off the inner surface 102. Exemplary paths of individual portions of this shock wave are indicated in FIG. 1. For example, acoustic energy traveling along paths 138 and 140 reflects off ellipsoidal surface 102 so as to travel paths 142 and 144, respectively. As is known in the are,t the use of an ellipsoidal inner surface allows energy emanating from one ellipsoidal focus to reflect off the ellipsoidal surface itself and be substantially refocused at the second, target focus 110 of the ellipsoid as can be seen by the convergence of pathways 142 and 144.

In the first embodiment of this ellipsoidal shock focus method (employing a bath 118 with sides 124), the shock waves travel directly from source focus 108 through a fluid medium 116 to penetrate the body-fluid interface 114 before converging in the neighborhood of target focus 110. In the second embodiment, the shock waves travel from a fluid medium 116 through a fluid 120 in the interior of shock transfer pad or body surface coupling belt 122 before penetrating the body-fluid interface 114.

i. Unpredictability and Uncontrollability of Peak Localization, Intensity, and Duration The ellipsoidal shock focus method has received approval from the Food and Drug Administration (FDA) in the United States. However, the ellipsoidal focus method has certain drawbacks and disadvantages. These drawbacks and disadvantages stem from the fact that ellipsoidal shock focus devices require the convergence of shock wave energy from a relatively large surface (truncated ellipsoid 102) to a small volume (near target focus 110).

For a variety of reasons, to be described immediately below, the focusing of shock energy into a small volume of body tissue is an uncertain and potentially dangerous science. First, the use of high explosives or electric arcs creates a supersonic shock wave whose characteristics are much less predictable and much less controllable than, for example, an analogously generated acoustic wave. Second, the velocity of a shock wave need not be constant, but may vary with the passage of time after the creation of the initial shock, and may vary with spatial direction based on asymmetries in the means of creating the shock source.

Furthermore, the incident angle of shock waves is not necessarily equal to the reflection angle of the shock waves, so that the mathematical model of reflection pathways off the ellipsoid itself may not be followed in practice.

The attempt of the ellipsoidal focus method to focus energy at a mathematical singularity point is further frustrated by the possible existence of thermal gradients along the shock wave pathway, nonuniform distribution of gas and mineral solutes in the liquid, and particulate suspensions.

The mathematical model of the ellipsoidal focus method involves the generation of a shock wave from a first mathematical singularity point and focusing the shock wave at a second mathematical singularity point. The practical considerations described above result in a focus of shock waves near the target focus 110 having properties tangibly at variance with the ideal mathematical model. The practical inability to achieve pinpoint localization results in variability and unpredictability in three important parameters: (1) localization of the focused shock waves; (2) peak intensity at the shock wave focus; and (3) duration of the focusing of shock waves.

Variability and unpredictability of the localization of the focused shock wave has apparently caused physical damage to the body tissue in the area of the target calculus. For example, treatment of kidney stones using this ellipsoidal focus method has commonly resulted in internal bleeding in the kidney, indicating that some of the shock wave pressure peaks were focused outside the target calculus, despite the use of expensive aiming equipment. The demonstrated presence of secondary injury apparently accompanies a failure to completely disintegrate target calculi in a significant number of patients, despite the application of 500–2000 "shots" of focused shock waves. Aiming accuracy is thus crucial to the success of the ellipsoidal focus disintegration effort.

The necessity of repeating shock wave treatments 500–2000 times indicates that the properties of shock wave focus provide only statistical, and not determinative, operation. The variability and unpredictability of shock wave focus localization, peak magnitude, and shock duration are apparently compensated for only by subjecting the patient to such a large number of "shots".

In addition to the bleeding resulting from secondary injury adjacent the target calculus, physical damage near the body-fluid interface 114 (FIGS. 1), as well as a second body-fluid interface 148 at the far side of the body, are issues of great concern, especially when dealing with shock wave repetitions of such quantity. In addition to the potential density discontinuities present at the body-fluid interfaces, the ESWL practitioner must be wary of gaseous bubbles 146 within the body 130 being treated. Such gaseous bubbles 146 may comprise the air within the alveoli of the lungs, as well as gases within the alimentary canal of the subject.

For reasons not yet completely understood, the use of the ellipsoidal shock focus method has resulted in permanent high blood pressure in certain patients.

Finally, patients undergoing treatments involving these 500-2000 shots must be placed under heavy anesthesia. Placement under heavy anesthesia is, in and of itself, an added risk which many patients cannot tolerate.

ii. Limitations on Quantitative Description

The variability and unpredictability of the localization, peak magnitude, and duration of the shock wave focus results in the lack of accurate quantitative description of the ESWL process. Quantitative descriptions of the process are highly desirable, since the effect of a given experiment or treatment could yield valuable information as to the quantity and magnitude of shock pulses necessary to safely disintegrate any given particular type of calculus. The lack of accurate quantitative description engenders a continued necessity to experiment with each individual patient, and each individual calculus type, sometimes resulting in potentially dangerous "overkill" treatments.

b. Focused Piezoelectric Array Method

Another method of extracorporeal shock wave lithotripsy is commonly used in France and Germany. This second method involves the generation of shock waves from a concave spherical surface whose inner face is covered with piezoelectric elements which are fired so as to produce converging shock waves which are focused in the target calculus. See, for example, U.S. Pat. No. 4,617,931 to Dory. This method, commonly referred to as the focused array method, does not produce as sharp a focus as the ellipsoidal shock wave focus method, described above. The focused array system reportedly has not caused the internal bleeding which is characteristic of the ellipsoidal focused shock wave method, and less anesthesia has been found necessary.

c. Electromagnetically Driven Piston Method

Another method of extracorporeal shock wave lithotripsy employs an electromagnetically driven water piston that generates a plane wave in a tube. An acoustic lens focuses the plane wave's acoustic energy on a target. See "Extracorporeal Shock Wave Lithotripsy: An Update" by Fuchs and Chaussy, *Endourology*, Vol. 2, No. 2, pp. 1-8 (1987).

d. Conclusion

It is therefore desirable to employ an ESWL device and method which overcome the disadvantages of focused shock waves which are used in known ESWL systems and methods. Elimination of the attendant dangers and uncertainties of individual treatment, as well as the lack of quantitative descriptions for future predictability of shock wave localization, peak magnitude, and duration, are also desirable goals for progress of extracorporeal shock wave lithotripsy.

SUMMARY OF THE INVENTION

The present invention overcomes the limitations of known ESWL systems described above by employing a shock wave which is a sector of a classical diverging spherical shock wave emanating radially from an effective point source in a non-focused but highly directional manner. A sector shock tube projects a "cap" shock whose leading spherical compression front and trailing rarefaction front define the means by which a target calculus is destroyed.

The cap shock's intensity, frontal area, and time duration may be accurately controlled by, for example, selection of effective explosive size, sector shock tube angle and length, and distancing of the sector shock tube from the target calculus.

The use of a classical spherical sector shock wave allows accurate, repeatable, quantitatively descriptive experiments and treatments to be performed. The non-focused nature of the cap shock eliminates the necessity for expensive aiming devices while ensuring calculus disintegration in a much smaller number of shock wave applications than in known focused shock wave methods. Entire calculi may be encompassed by the compression and rarefaction shock fronts of a single cap shock so that the calculus as a whole is disintegrated, rather than being "chipped apart" by the more localized, "pinpoint" focused shock waves known in the art.

The rarefaction front, which defines the width and duration of the cap shock, also provides controllable means for minimizing risk of damage to body tissue, both along the path of the cap shock and remote from it, particularly at air-tissue interfaces.

BRIEF DESCRIPTION OF THE DRAWINGS

The invention is best understood by reading the following detailed description in conjunction with the following drawings, in which like reference numbers refer to like elements throughout, and in which:

FIG. 4 illustrates the longitudinal physical propagation of the "cap shock" produced by the sector shock tube according to the present invention.

FIGS. 5A, 5B, and 5C illustrate the diverging, critical, and converging loci of the cap shock edge as a function of various cone parameters.

FIGS. 6A and 6B illustrate shock wave intensity as a function of distance from the shock source for the ellipsoidal-focus method, and for the preferred embodiment of the conical sector shock tube according to the present invention, respectively.

DETAILED DESCRIPTION OF THE PREFERRED EMBODIMENTS

1. Conical Sector Shock Tubes

The use of a high explosive near the apex of a conical shock tube is known in the art. See, for example, U.S. Pat. No. 3,184,955. Also, substantially conical shock wave beaming or channeling elements have been used in seismic prospecting techniques. See, for example, U.S. Pat. No. 3,275,098. Also, conical shock wave beaming or channeling devices have been employed in directional ranging applications. See, for example, U.S. Pat. No. 3,521,725. These U.S. patents name the same inventor as the present inventor.

a. Amplification Effect

Figure 2:
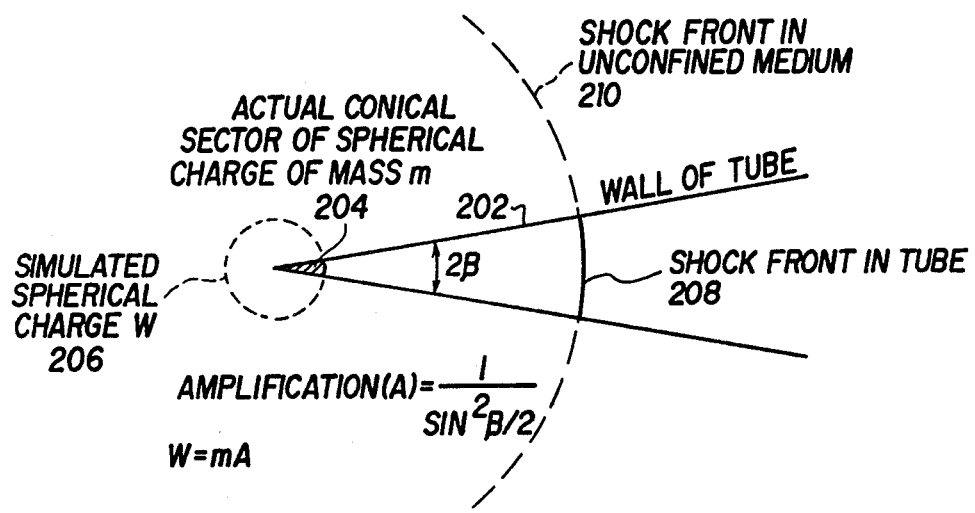
FIG. 2 demonstrates the amplification factor A which is characteristic of the use of the conical sector shock tube according to the present invention.

Referring now to FIGS. 2, a conical tube 202 is indicated schematically. Of course, FIG. 2 can only represent the sector shock tube according to the preferred embodiment of the present invention in two dimensions, i.e., as two diverging lines. However, it is to be understood that in three dimensions the preferred embodiment of the sector shock tube is conical, whose intersection with a plane containing the axis of the cone appears as in FIG. 2.

Throughout this discussion, reference will be made to a high explosive charge of mass m. However, it should be understood that other means of producing a shock wave, such as electric arcs or laser energy, may be employed. The charge of mass m is located at the apex of cone 202 so as to simulate a conical sector of an imaginary spherical charge 206. In this way, for a sector shock tube whose angle is $2*\beta$, an amplification factor A of $1/\sin^2(\beta/2)$ is achieved. That is, by employing a charge of mass m, a shock front 208 within the sector shock tube is created which is a sector of a classical diverging spherical shock wave 210 in an unconfined medium which would be produced by explosion of a spherical charge of mass $W=mA$.

In practice, energy losses occur near the time of detonation. Calculations predicting shock parameters and cap shock configuration must therefore employ an efficiency factor with m that is in the range of approximately 0.25 to 0.35. The efficiency factor for a particular cone-charge configuration may be established from shock pressure measurements and the use of scaling laws.

b. Generation of the "Cap" Shock

Henceforth, this discussion will focus on only the shock front 208 as it projects outwardly from sector shock tube 202 in a non-focused manner along the axis of rotation of the conical sector shock tube. The means by which the sector of a classical diverging spherical shock wave is created and projected by the preferred embodiment is illustrated in a timewise sequence in FIGS. 3A, 3B, 3C, and 3D.

Figure 3A:
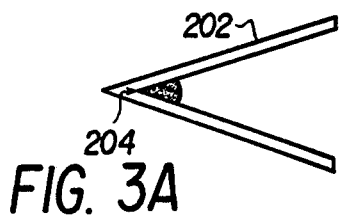
FIGS. 3A, 3B, 3C and 3D indicate the temporal sequence in which a shock wave comprising a sector of a classical diverging spherical shock wave may be produced and projected beyond the end of the conical shock tube according to the preferred embodiment of the present invention.

Referring to FIG. 3A, the conical sector shock tube 202 is illustrated with an as yet unexploded charge of high explosive 204.

Figure 3B:
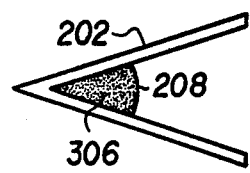

FIG. 3B illustrates in shaded area 306 the area of compression generated immediately after the explosion of charge 204. At the leading surface of the shaded compressional area is the compressional front 208. The compressional front propagates away from the apex of the sector shock tube 202.

When the compression front 208 produced by the explosion of charge 204 propagates beyond the rim 312 of sector shock tube 202, a diffractive effect is produced. In conformance with principles generally understood in wave physics, the propagation of a wave such as compression front 208 past the rim 312 of a surface 202 produces a rarefaction front 314. Rarefaction front 314 propagates away from the rim 312 to manifest the diffraction effect.

Figure 3C:
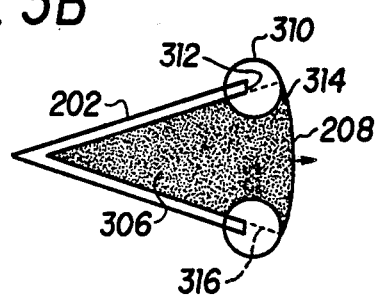
Figure 3D:
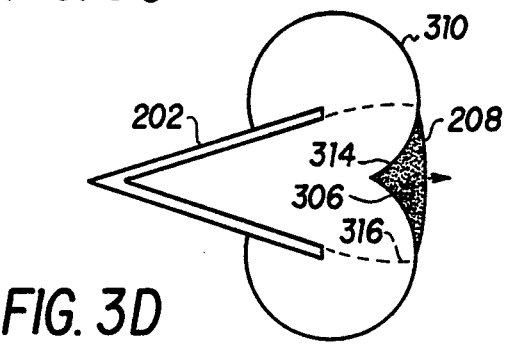

In the case of circular rim 312 which is defined by the cone-shaped sector shock tube 202, the rarefaction front defines a substantially toroidal expanding rarefaction volume indicated generally by element 310 (FIGS. 3C, 3D). As compression front 208 continues to propagate away from the apex of the sector shock tube 202, the rarefaction front 314 also continues to expand behind the compression front 208. Although no negative pressures are actually produced using this configuration, the portion of the compression zone indicated in shaded area 306 is continuously eroded as the rarefaction front 314 "chases" the compression front 208.

FIG. 3D indicates the continued erosion of the compression zone 306 as the rarefaction front 314 from opposite sides of the sector shock tube 202 have overlapped one another. Once the opposing rarefaction fronts 314 overlap one another, the zone 306 of high compression continues to propagate away from the sector shock tube. This zone 306 of high compression is referred to as the "cap shock".

The cap shock propagates in a manner illustrated in FIG. 4. A single cap shock is illustrated at successive instants of time as elements 420, 430, and 440 in FIG. 4. In an actual scenario, a single cap shock would be generated and would propagate through the target area and be dissipated long before the next cap shock would be created.

c. Quantitative Control of Cap Shock Parameters

The mathematical model which describes the properties of the cap shock as it propagates along the line of projection along the axis of rotation 450 of the sector shock tube 202, being continually eroded by the rarefaction front emanating from sector shock tube edge 312, is well understood in the art. See, for example, Coombs and Thornhill, "An Underwater Explosive Shock Gun," *J. Fluid Mech.*, Vol. 29, Part 2, pp. 373–83 (1967), which is incorporated herein by reference.

Generally, the parameters of interest to the designer of a sector shock tube used in ESWL applications according to the present invention include the following.

i. Cap Shock Intensity

The first parameter of interest is the cap shock intensity. The strength of the compression front, and the degree of cap shock erosion produced by the rarefaction front, are determined by the amount of charge to be placed at the apex of sector shock tube 202, the angle and length of the sector shock tube. Optimization of the compression wavefront magnitude and rarefaction progression allows shock wave energy to be directed at the target calculus which is of sufficient magnitude to disintegrate it, while still protecting surrounding body tissue from damage.

ii. Cap Shock Directionality

The second parameter of interest in ESWL applications of the sector shock tube is the directionality of the cap shock propagation. It is one of the major advantages of the present invention that the crucial aiming requirements of known ellipsoidal focus methods may be substantially relaxed when employing a sector of a classical spherical diverging shock wave. Known focused shock wave methods depend on critical aiming accuracy (down to millimeters) in order to prevent secondary injury or even to have the known device succeed in disintegrating the calculus. In contrast, the present invention's relaxed aiming precision tolerances (in centimeters) result from the fact that a cap shock is employed which (at the target site) may have lower pressure than the peak pressure of known focused shock methods. Thus, the expensive X-ray or acoustical target locating and shock source or patient positioning methods that are essential for ellipsoidal focus devices are not necessary for the practice of the present invention, either for prevention of secondary injury or for disintegration of the target calculus. These may be replaced by simpler, less expensive means when practicing ESWL according to the present invention.

iii. Cap Shock Duration

A third parameter of interest is the effective time duration of the cap shock as experienced by the target calculus. This time duration is defined by the distance between the compression and rarefaction fronts, such as 448 and 44, respectively (FIG. 4), divided by the velocity of the shock wave. This parameter is important because it relates to the total energy available in the wave. The leading compression front 448 and the trailing rarefaction front 444 are involved in the weakening of the target calculus as a whole. The target calculus is thus disintegrated in much fewer shock repetitions than in the focused shock methods known in the art.

iv. Cap Shock Width

Finally, the fourth parameter of interest is the width of the cap shock, as defined by the intersection of the spherical-sector compression fronts 428, 438, and 448 with the expanding spherical diffraction-caused rarefaction fronts 424, 434, and 444, respectively. The intersection of these two fronts, indicated as circular loci 426, 436, and 446, follow a path 316 which is highly predictable and controllable, as will be seen immediately below.

v. The Intersection Locus

FIG. 5 illustrates the theoretical intersection loci for various cone parameter conditions, as described in greater detail in the article by the present inventor, "Shock Beaming Capabilities of Hydrodynamic Conical Shock Tubes," *The Journal of the Acoustical Society of America*, Vol. 50, No. 5 (Part 2), pp. 1313–1320 (1971) (discussion related to FIG. 2 in that article). See also Coombs and Thornhill, *J. Fluid Mech.*, referenced above. These articles are incorporated herein by reference.

Basically, the locus of intersection of compression and rarefaction fronts follows a path which may be diverging (FIG. 5A), critical (essentially cylindrical) (FIG. 5B), or converging (FIG. 5C). Whether the locus is diverging, critical, or converging is a function of the effective mass m of the charge used, the length b of the sector shock tube (distance between the apex and the rim), and $2*\beta$ (the cone angle). For reasons which will be apparent upon a reading of the discussion of FIGS. 6A and 6B, below, the converging locus of FIG. 5C is especially suited for ESWL applications.

The above-mentioned articles present a description of the known physics involved to a degree which would enable one skilled in the art to apply the quantitative principles of sectors of classical diverging spherical shock waves to the problem of disintegrating target calculi such as kidney stones or gallstones.

d. Contrast with Focused Shock Wave Methods

The present invention functions substantially differently than the ellipsoidal focus method described above. The method employing focused shock waves functions like a sharp instrument attempting to chip away at a target calculus by sustained repetition of extremely localized ("pinpoint") shock wave energy, analogous to an ice pick. Although this known method chips and cracks the calculus into smaller and smaller fragments through the sustained repetition of shock wave applications, the overall compressive and tensile strength of the remaining fragments is left substantially unaffected.

In contrast, the present invention's cap shock, whose width may advantageously be larger than the diameter of the calculus itself, weakens the compressive and tensile strength of the target calculus as a whole, resulting in disintegration of the target calculus in a much loser quantity of shock wave repetitions. The reduction in the compressive and tensile strength of the target calculus is observed when the incident compression front 448 (FIG. 4) is followed by the substantial reduction in pressure (though not actual negative pressure) of the rarefaction front 444. Instead of chipping away at minute fragments of the calculus, the cap shock according to the present invention pulverizes the entire calculus.

The mechanism for aiming of the sector shock tube at the target calculus need not be as accurate as was required of known focused shock wave devices. This relaxation of aiming constraints follows from the fact that, in the preferred embodiment, the target calculus is ½–⅔ths the width of the cap shock. Furthermore, since the locus of the intersection of the compression and rarefaction fronts may be controlled using formulas from the earlier referenced work by Coombs and Thornhill describing the, the danger of secondary injury can be minimized, for example, by causing the locus to converge (so that the cap shock disappears) before the cap shock exits the body.

The cap shock according to the present invention can easily be controlled to use a compression front pressure, cap shock duration, and cap shock diameter (about 25 mm in most practical scenarios) that need never exceed the minimum necessary to disintegrate the target calculus.

It is one of the drawbacks of known focused shock wave methods that it is uncertain exactly what the peak pressure of the focused shock wave method is at the target site. The peak focused shock wave intensity is said to be controllable from about 5,000 psi to 50,000 psi.

However, one set of measurements for a single setting of the system showed pressure ranging in almost random fashion from 3,000 to 8,000 psi over 800 shots. (See Hunter et al., "Measurement of Shock Wave Pressures Used for Lithotripsy," *The Journal of Urology*, Vol. 136, pp. 733–738 (1986).) Furthermore, the absolute value of these measurements is subject to question, due to the relatively large measurement probe used in the experiments. An unduly large experiment probe results in an effective "averaging" of the actual peak pressure with other, lower pressures present throughout the measurement probe area. Therefore, the actual peak pressure (presumably the pressure which causes damage to surrounding the tissues if the aiming mechanism misfunctions or the shock wave energy is for some other physical reason misdirected) may actually be several times higher than this measured "average" peak pressure. Indeed, pressures several times larger have been reported for conditions similar to that of Hunter et al. (see Chaussy, Ch. (ed.), *Extracorporeal Shock Wave Lithotripsy*, Karger, 1982, 1986, pp. 11, 19).

In contrast, the present invention's use of a sector of a classical diverging spherical wave front whose properties are controllably repeatable allows its peak pressure to be reliably produced to within 10% tolerance. Thus, for example, where the target calculus is of a type known to have a lower compressional and tensile strength, cap shocks of correspondingly lower intensity may be employed so as to avoid needless risk of secondary injury.

The shock wave nominal operating intensity of the present system's cap shock (about 8,000–12,000 psi at the calculus and about 40% higher at the body-fluid interface) is in the low to mid-range of the known ellipsoidal-focused method. The present invention's reduction in the number of shock wave repetitions necessary to disintegrate the calculus (possibly on the order of 1–10 cap shocks versus 500–2000 ellipsoidally focused shock waves) implies that there is less danger of damage to body tissue at the body-fluid interface than with the known system.

Figure 1:
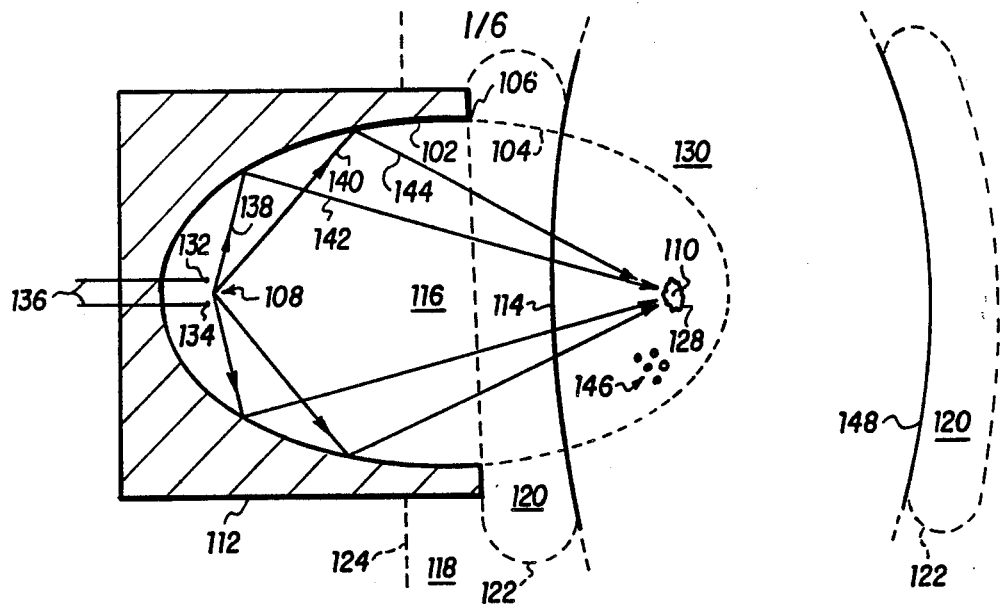
FIG. 1 represents a cross-sectional view of a known ellipsoidal shock wave focus device.

The difference in shock wave intensity as a function of time is schematically illustrated in FIGS. 6A and 6B. FIG. 6A shows, as a function of distance from the source focus (element 108 of FIG. 1) the intensity of shock waves produced by the ellipsoidal shock wave focus device known in the art. After a shock source is activated at source focus 108, the intensity of the shock wave drops off rapidly until the shock waves impact the inner surface 102 of the truncated ellipsoidal reflector. After striking the inner surface of the truncated ellipsoidal reflector (indicated in FIG. 6 as a single point 604 for simplicity), the shock waves begin to converge. The shock waves penetrate the body-fluid interface 608 to reach a peak 610, preferably (but not reliably) in the target calculus 128 (FIG. 1). To the right of peak 610, the shock waves again defocus, so that the shock wave intensity 612 at body-fluid interface 148 has been reduced in magnitude as compared with its peak value at 610.

FIG. 6B shows shock wave intensity of the preferred embodiment of the present invention as a function of distance from the apex of the conical sector shock tube. Following known rules of shock wave physics, the shock wave intensity of a sector of a classical spherical diverging shock wave decreases in magnitude as a function of distance from the apex of the sector shock tube, as indicated by line 614. The cap shock penetrates the body-fluid interface at point 616 and the target calculus at 618.

In the preferred embodiment, conical sector shock tube parameters are chosen so as to produce a converging locus (FIG. 5C). When the rarefaction front from the rim of the sector shock tube converges with the compression front, then the cap shock "disappears" (i.e., experiences a sudden decrease in magnitude), as indicated at 620. Therefore, when the completely eroded cap shock encounters body-fluid interface 148, its magnitude has been substantially reduced, as indicated at 622.

A comparison of FIGS. 6A and 6B show the substantial difference in the manner of operation of the two devices. Although in practical scenarios the magnitude of the spherical-sector shock wave at body-fluid interfaces 616 and 622 may be greater than the shock wave intensities of the ellipsoidal focused shock wave method at 608 and 612, respectively, the greatly reduced number of repetitions necessary to pulverize target calculus results in an overall reduction in the risk of secondary injury at the body-fluid interfaces 114 and 148. The intensity of the cap shocks as they enter the body at 616 are still well within safety tolerances (provided, of course, that the normal precautions against density discontinuities such as air bubbles and particle suspensions are taken).

Furthermore, the substantial reduction in the magnitude of the spherical sector shock wave at the target calculus 618 as compared with the comparatively unpredictable high-intensity shock wave focus 610 of the ellipsoidal focus method helps to prevent secondary injury in the neighborhood of the target calculus.

Therefore, considering either the body-fluid interface, or the body tissue in the immediate vicinity of the target calculus, practical embodiments of the present invention expose the patient to a substantially reduced risk of secondary injury.

e. Practical Physical Embodiment

Figure 7:
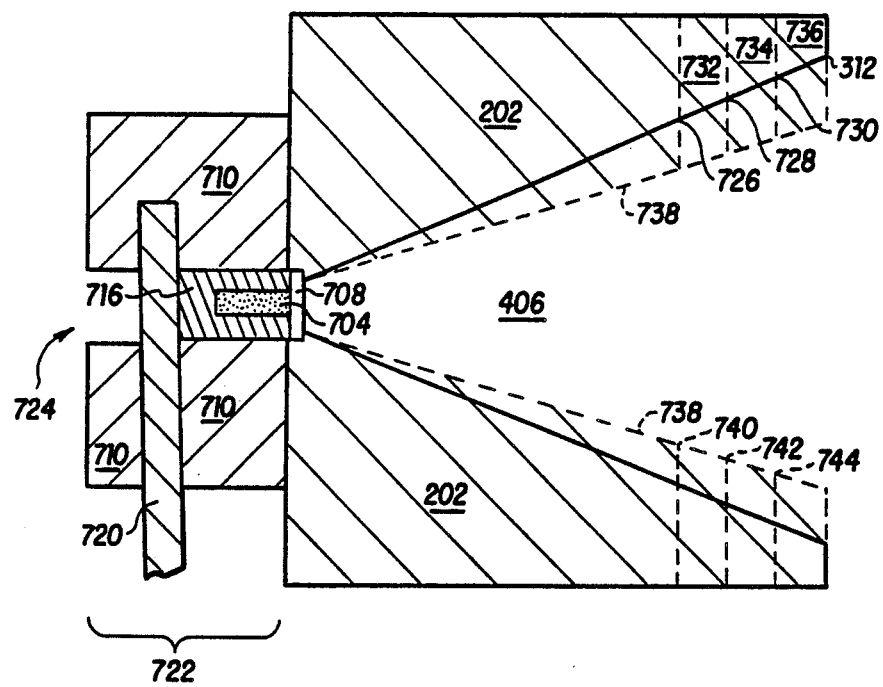
FIG. 7 illustrates in a cross-sectional view the preferred embodiment of the high explosive shock wave energy source which may be employed with preferred sector shock tubes according to the present invention.

FIG. 7 illustrates a cross-sectional view of a practical embodiment of the ESWL device according to the preferred embodiment of the present invention.

The major components of the system are the sector shock tube 202 (described above) and the firing block 722 (to be described in greater detail below).

Sector shock tubes should be fabricated with a wall thickness that far exceeds strength requirements. This design satisfies an overriding requirement for rigidity under the high stress caused in the interior of the shock tube. It has been found that shock tube wall deflection must not exceed approximately 0.001 inch if dissipation of shock strength along the inner surface of the shock tube is to be avoided.

Briefly, firing block 722 comprises a firing block housing 710 into which is fitted an explosive charge assembly. This explosive charge assembly includes a shock mitigator sleeve 716 that is designed to fit around a high explosive charge 704 inserted in the sleeve. Although not explicitly shown in FIG. 7, an electric exploding bridge wire, as commonly used in the art, is attached to high explosive charge 704 to cause its detonation. Optionally, at the front of the charge 704 may be a bulkhead, or shock transmission plate 708.

A sliding breech 720 facilitates the insertion of the high explosive charge, or alternatively, an entire explosive charge assembly, through an opening 724 in the housing 710.

In an alternate embodiment, the charge element 704 is replaced by a type of sealed initiator (described in detail in "Feasibility Study of a Fail-Safe Through Bulkhead Initiator," A.C. Schwarz, Sandia Laboratories, New Mexico, SAND 78-1696, March, 1980) which transmits a strong shock wave to the water through a steel plate that is part of the initiator, but which is not ruptured by the shock wave during operation. Such initiators have long been a part of inventory for use as solid rocket igniters for the Department of Defense and NASA.

Advantageously, a magazine arrangement such as might be used in known ESWL systems, or even weapon systems, may be adapted for use in the rapid insertion of a series of high explosive charges 704, or perhaps a series of entire explosive charge assemblies 704/708/716. An advantage of the present invention over known systems is the reduction in the requirement for a large number of successively applied shock waves. By implication, the need for expansive and potentially failure-prone "rapid fire" loading systems is avoided.

Figure 8:
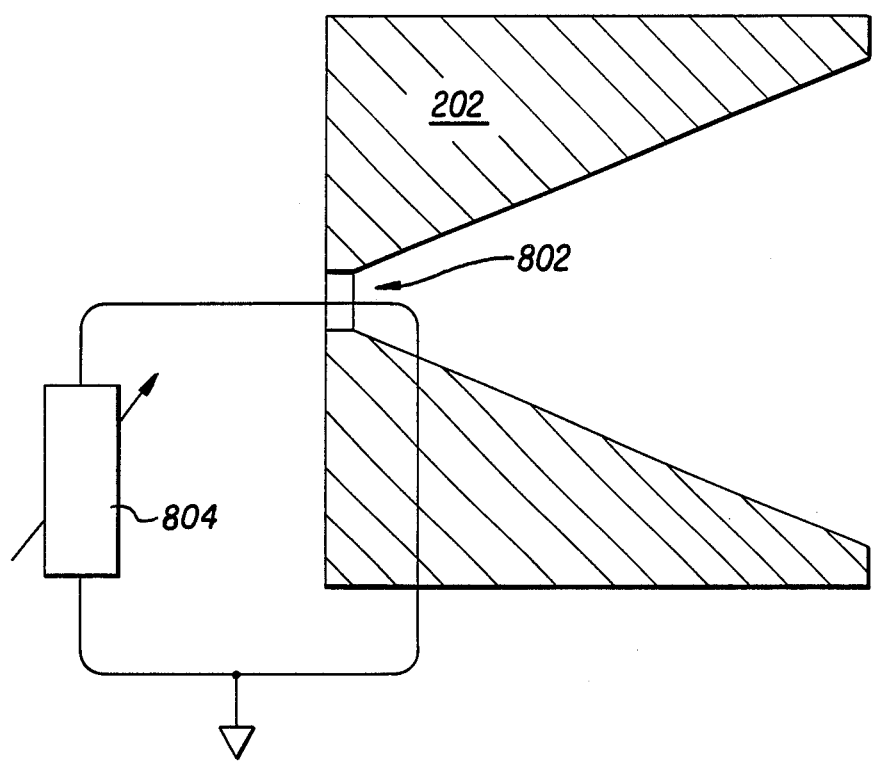
FIG. 8 illustrates a cross-sectional view in schematic form an apparatus for producing a gas generating arc reaction in a sector shock tube 202 according to a preferred embodiment of the present invention, utilizing a known adjustable energy source 804 as a subcomponent.

It should be understood that the use of a high explosive charge is but one example of a shock wave source. For example, a gas generating arc reaction, caused by electrodes 802 (FIG. 8) inserted in a small chamber at the effective apex of the sector shock tube 202 could be used to generate the sector shock. A shock intensity adjustor (such as one known in the art and traditionally used with ellipsoidal-focus apparatus) is indicated schematically as comprising element 804 in conjunction with electrodes 802 (FIG. 8) in use with a sector shock tube. Alternatively, a laser device, as commonly employed in the art, may be employed as an initiation means, or as the entire energy source.

Although embodiments of the present invention require much fewer shock wave applications than known ellipsoidal focusing devices, it is known that, over time, successive explosions within a closed space (such as the chamber occupied by high explosive 704) may cause deformation in the surrounding materials. To extend the useful life of the implementations of the present invention, the expendable shock mitigator sleeve 716 is employed. The shock mitigation material may be any porous metal, such as 50% porous copper. The shock mitigation material absorbs the shock energy, thereby cushioning the surrounding metallic material in firing block housing 710.

During operation, the shock source, such as high explosive 704, is detonated, causing a shock wave to be transmitted through optional bulkhead 708 and into fluid transmission medium 406, such as, for example, degassed water. In embodiments where replaceable high explosive charges 704 are employed, the optional bulkhead (or shock transmission plate) 708 also serves as an operational and safety seal to prevent gas or particles from the explosive 704 from moving downstream.

As will be described in greater detail in the subsections below, with special reference to FIG. 7, the present invention envisions application of a single adjustable apparatus to treatment of a variety of hardened accumulations. Thus, a method of treating any of a variety of hardened accumulations in one or more living patients' bodies, may comprise the steps of choosing a shock source of a first magnitude, and a sector shock tube of a first angle and first length; generating a first sector of a classical diverging spherical shock wave so as to channel the first sector in a non-focused but directional manner substantially through a first hardened accumulation; choosing a shock wave source of a second magnitude, and a sector shock tube of a second angle and second length; and generating a second sector of a classical diverging spherical shock wave so as to channel the second sector in a non-focused but directional manner substantially through a second hardened accumulation. At least one of the second magnitude, angle and length is different than a respective one of the first magnitude, angle and length.

i. Variability of Shock Source Power

Advantageously, the preferred embodiment of the present invention makes use of the high degree of controllability and predictability of the sector shock wave by allowing high explosive charges of various explosive power to be selectively employed in a single device. To this end, the chamber into which high explosive charge 704 is loaded is advantageously capable of receiving and detonating high explosive charges of various sizes, corresponding to the desired shock wave intensity needed for disintegration of a particular target calculus. Larger amounts of high explosive would occupy a greater volume of the chamber, correspondingly reducing the volume which need be occupied by shock mitigator sleeve 716.

ii. Variability of Shock Tube Length

As was described in the above-referenced article by Coombs and Thornhill, the intersection locus for the compression and rarefaction waves is also dependent on the distance from the rim 312 of sector shock tube 202 to its apex. To make use of this ability to accurately and predictably control the intersection locus (and therefore to control the width and duration of the cap shock), the preferred embodiment of the present invention envisions a set of removable supplementary rims, three of which are indicated installed at 732, 734, and 736 (FIG. 7). The insertion or removal of these supplementary rims effects a change in the diffractive characteristics of sector shock tube 202 so that the intersection locus is modified for the particular EWSL application according to well-understood principles. Preferably, the supplementary rims 732, 734, and 736 should fit snugly against the basic sector shock tube 202 so that no diffractive effects are present at joints 726, 728, and 730.

To effect such a change in shock tube length, the entire sector shock tube 202 could also be removably attached to firing block housing 710 (and optional bulkhead 708). Alternatively, the sector shock tube may be augmented with a single supplementary rim taken from a family of supplementary rims. For instance, if an apex-rim distance to rim 730 were desired, a single supplementary rim of thickness equaling the sum of the thickness of rims 732 and 734 could be employed.

iii. Variability of Shock Tube Angle

As described in the above-referenced article by Coombs and Thornhill, the intersection locus for the compression and rarefaction waves is also dependent on the angle $\beta$ of the sector shock tube 202. To make use of this ability to accurately and predictably control the intersection locus (and therefore to control the width and duration of the cap shock), the preferred embodiment of the present invention envisions a set of one or more removable cone inserts, one of which is indicated installed at 738 (FIG. 7). The insertion or removal of this cone insert effects a change in the characteristics of the sector shock tube 202 so that the intersection locus is modified for the particular ESWL application according to well-understood principles. Preferably, the cone insert 738 should fit snugly inside the basic sector shock tube 202 so that no outward deflections of the cone insert/sector shock tube are experienced during the production of a shock wave.

To effect such a change in shock tube angle, entire sector shock tubes 202 of various chosen angles $\beta$ could also be removably attached to firing block housing 710 and bulkhead 708. Preferably, the sector shock tube 202 is augmented by only a single cone insert taken from a family of cone inserts, so as to avoid the problem of fitting one cone insert within another cone insert.

Of course, the present invention envisions adjustability of both the supplementary rims 732, 734, and 736 in conjunction with cone inserts such as 738. The simultaneous adjustability of the cone length (by addition of supplementary rims) as well as cone angle (by using a cone insert), when coupled with the flexibility in choosing shock source magnitude, provide the user with substantially total control over the quantitative characteristics of the cap shocks produced.

iv. Auxiliary Functions

The various other components of a system necessary for the successful treatment of concretions such as kidney stones or gallstones include such elements as locating systems, positioning systems, and control and firing systems.

Locating systems generally serve the function of finding where the target calculus is located within the body of the patient. Commonly used locating systems, include X-ray system, as well as ultrasonic systems. See, for example, U.S. Pat. No. 4,608,979 to Breidenthal, Lotz and Russel. Such locating systems are understood in the art, and will not be further detailed here.

Positioning systems serve the purpose of taking information gained from the locating system, described above, and position the axis of the sector shock wave tube at the right point, and at the right distance, from the target calculus. Devices such as this are known in the art, and will not be further described here.

Standard control and firing systems, by which (once the calculus has been located by the locating system, and the patient and the sector shock tube have been properly positioned with respect to one another) the firing of the shock waves at the target calculus is effectuated, may be employed. As with the locating and positioning system, the control and firing systems required to make the present invention function in a practical embodiment are known in the art, and will not be further described here.

2. Conclusion

Whereas various embodiments of the present invention have been described above, it should be understood that they have been presented by way of example, and not limitation. Thus, the breadth and scope of the present invention should not be limited by any of the abovedescribed exemplary embodiments, but should be defined only in accordance with the following claims and their equivalents.

What is claimed is:

1. An apparatus for treating one or more hardened accumulations in the body of a living patient, comprising:
   a source of shock wave energy, said energy being greater than a predetermined magnitude;
   a sector shock tube, connected to said source, for generating sectors of classical diverging spherical shock waves from the shock wave energy generated by said source, one or more supplementary rims mounted on said sector shock tube whereby the width and duration of said sectors are determined, said sector shock tube comprising a surface adapted for channelling said sectors in a non-focused but directional manner into the body of the patient; said predetermined magnitude being large enough so that when said surface channels said sectors, said sectors comprise sufficient shock wave energy to disintegrate the hardened accumulation; and
   a coupling means adapted to be disposed between said sector shock tube and the body of the living patient, through which said sectors are channeled for transmitting shock wave energy between said sector shock tube and the body of the patient.

2. The apparatus of claim 1, wherein:
   said sector shock tube comprises a cone at whose apex is located said source of shock wave energy.

3. An apparatus for treating one or more hardened accumulations in the body of a living patient, comprising:
   a source of shock wave energy, said energy being greater than a predetermined magnitude;
   sector shock tube means, connected to said source, for generating sectors of classical diverging spherical shock waves from the shock wave energy generated by said source, said sector shock tube means having characteristics chosen to produce converging compression-rarefaction intersection loci, and said shock waves having cap shocks whose trailing fronts are rarefaction fronts formed by rarefaction effects at least partially determined by the characteristics of said sector shock tube means;
   one or more supplementary rims mounted on said sector shock tube means whereby the width and duration of said sectors are determined, said sector shock tube means comprising a surface adapted for channelling said sectors in a non-focused but directional manner into the body of the patient;
   said predetermined magnitude being large enough so that when said surface channels said sectors, said sectors comprise sufficient shock wave energy to disintegrate the hardened accumulation; and
   a coupling means adapted to be disposed between said sector shock tube means and the body of the living patient, through which said sectors are channelled for transmitting shock wave energy between said sector shock tube means and the body of the patient.

4. An apparatus for treating one or more hardened accumulations in the body of a living patient, comprising:
   means for providing a source of shock wave energy, said energy being greater than a predetermined magnitude;
   means for varying the intensity of said shock wave energy;
   a sector shock tube, connected to said source, for generating sectors of classical diverging spherical shock waves, said sector shock tube comprising a surface adapted for channelling said sectors in a non-focused but directional manner into the body of the patient; said predetermined magnitude being large enough so that when said surface channels said sectors, said sectors comprise sufficient shock wave energy to disintegrate the hardened accumulation; and
   a coupling means adapted to be disposed between said sector shock tube and the body of the living patient, through which said sectors are channelled for transmitting shock wave energy between said sector shock tube and the body of the patient.

5. An apparatus for treating one or more hardened accumulations in the body of a living patient, comprising:
   means for providing a source of shock wave energy said energy being greater than a predetermined magnitude;
   means for varying the intensity of said shock wave energy;
   sector shock tube means, connected to said source, for generating sectors of classical diverging spherical shock waves from the shock wave energy generated by said source, said sector shock tube means having characteristics chosen to produce converging compression-rarefaction intersection loci, and said shock waves having cap shocks whose trailing fronts are rarefaction fronts formed by rarefaction effects at least partially determined by the characteristics of said sector shock tube means;

said predetermined magnitude being large enough so that when said surface channels said sectors, said sectors comprise sufficient shock wave energy to disintegrate the hardened accumulation; and a coupling means adapted to be disposed between said sector shock tube means and the body of the living patient, through which said sectors are channelled for transmitting shock wave energy between said sector shock tube means and the body of the patient.

6. An apparatus for treating one or more hardened accumulations in the body of a living patient, comprising:

a source of shock wave energy, said energy being greater than a predetermined magnitude;

a sector shock tube, connected to said source, for generating sectors of classical diverging spherical shock waves from the shock wave energy generated by said source, one or more angle adjustment inserts mounted on said sector shock tube whereby the width and duration of said sectors are determined, said sector shock tube comprising a surface adapted for channelling said sectors in a non-focused but directional manner into the body of the patient;

said predetermined magnitude being large enough so that when said surface channels said sectors, said sectors comprise sufficient shock wave energy to disintegrate the hardened accumulation; and a coupling means adapted to be disposed between said sector shock tube and the body of the living patient, through which said sectors are channelled for transmitting shock wave energy between said sector shock tube and the body of the patient.

7. The apparatus of claim 6, wherein:

said sector shock tube comprises a cone at whose effective apex is located said source of shock wave energy; and said one or more angle adjustment inserts fit snugly in the interior of said sector shock tube.

8. An apparatus for treating one or more hardened accumulations in the body of a living patient, comprising:

a source of shock wave energy, said energy being greater than a predetermined magnitude;

a sector shock tube means, connected to said source, for generating sectors of classical diverging spherical shock waves from the shock wave energy generated by said source, said sector shock tube means having characteristics chosen to produce converging compression-rarefaction intersection loci, and said shock waves having cap shocks whose trailing fronts are rarefaction fronts formed by rarefaction effects at least partially determined by the characteristics of said sector shock tube means;

one or more angle adjustment inserts mounted on said sector shock tube means whereby the width and duration of said sectors are determined, said sector shock tube means comprising a surface adapted for channelling said sectors in a non-focused but directional manner into the body of the patient;

said predetermined magnitude being large enough so that when said surface channels said sectors, said sectors comprise sufficient shock wave energy to disintegrate the hardened accumulation; and a coupling means adapted to be disposed between said sector shock tube means and the body of the living patient, through which said sectors are channelled for transmitting shock wave energy between said sector shock tube means and the body of the patient.

9. A method of treating one or more hardened accumulations in the body of a living patient, comprising the steps of:

positioning a shock wave generator with respect to the patient's hardened accumulation; and generating one or more sectors of a classical diverging spherical shock wave so as to channel said one or more sectors in a non-focused but directional manner substantially through said hardened accumulation so as to substantially reduce its tensile and compressional strength, whereby said hardened accumulation may be destroyed.

10. The method of claim 9, wherein said generating step comprises:

generating an explosion at the effective apex of a cone structure comprising at least a portion of the shock wave generator, to channel said one or more sectors out an open end of said cone structure away from said apex.

11. The method of claim 10, further comprising the step, performed before said positioning step, of:

choosing an explosion magnitude, cone angle and cone length so as to substantially optimally destroy the hardened accumulation without causing secondary injury to the patient.

12. A method of treating any of a variety of hardened accumulations in one or more living patients' bodies, comprising the steps of:

choosing a shock source of a first magnitude, and a sector shock tube of a first angle and first length;

generating a first sector of a classical diverging spherical shock wave so as to channel said first sector in a non-focused but directional manner substantially through a first hardened accumulation;

choosing a shock wave source of a second magnitude, and a sector shock tube of a second angle and second length; and generating a second sector of a classical diverging spherical shock wave so as to channel said second sector in a non-focused but directional manner substantially through a second hardened accumulation;

wherein at least one of said second magnitude, angle and length is different than a respective one of said first magnitude, angle and length.

13. An apparatus for treating one or more hardened accumulations in the body of a living patient, comprising:

a source of shock wave energy, said energy being greater than a predetermined magnitude;

a sector shock tube, connected to said source, for generating sectors of classical diverging spherical shock waves from the shock wave energy generated by said source, said sector shock tube comprising a surface adapted for channelling said sectors in a non-focused but directional manner into the body of the patient;

said predetermined magnitude being large enough so that when said surface channels said sectors, said sectors comprise sufficient shock wave energy to disintegrate the hardened accumulation; and a coupling means adapted to be disposed between said sector shock tube and the body of the living patient, through which said sectors are channelled for transmitting shock wave energy between said sector shock tube and the body of the patient.

14. An apparatus for treating one or more hardened accumulations in the body of a living patient, comprising:

a source of shock wave energy, said energy being greater than a predetermined magnitude;

a cone-shaped sector shock tube, connected to said source,e for generating sectors of classical diverging spherical shock waves from the shock wave energy generated by said source, said sector shock tube having a cone-shaped interior surface adapted for channelling said sectors in a non-focused but directional manner into the body of the patient;

said predetermined magnitude being large enough so that when said surface channels said sectors, said sectors comprise sufficient shock wave energy to disintegrate the hardened accumulation; and a coupling means adapted to be disposed between said sector shock tube and the body of the living patient, through which said sectors are channeled for transmitting shock wave energy between said sector shock tube and the body of the patient.

* * * * *